US005824494A

United States Patent [19]
Feldberg

[11] Patent Number: 5,824,494
[45] Date of Patent: Oct. 20, 1998

[54] METHOD FOR ENUMERATING BACTERIAL POPULATIONS

[75] Inventor: Simon Feldberg, Rehovot, Israel

[73] Assignee: Sirotech Ltd., Ness Ziona, Israel

[21] Appl. No.: 429,340

[22] Filed: Apr. 26, 1995

[30] Foreign Application Priority Data

May 1, 1994 [IL] Israel ........................................ 109492

[51] Int. Cl.⁶ .................................................... C12Q 1/08
[52] U.S. Cl. ........................... 435/40; 435/30; 435/288.4; 324/446; 324/450
[58] Field of Search ................................. 435/29, 30, 31, 435/32, 34, 39, 40, 287.1, 288.4, 288.5, 305.2, 305.3, 817; 422/82.01, 82.02; 436/150; 324/442, 444, 450, 663, 674, 681, 692, 707, 71.1, 446

[56] References Cited

U.S. PATENT DOCUMENTS

| | | |
|---|---|---|
| 3,743,581 | 7/1973 | Cady et al. . |
| 3,890,201 | 6/1975 | Cady . |
| 4,018,652 | 4/1977 | Lanham et al. ............................ 435/40 |
| 4,072,578 | 2/1978 | Cady et al. . |
| 4,160,205 | 7/1979 | Hobbs et al. ......................... 435/287.1 |
| 5,187,096 | 2/1993 | Giaever et al. .......................... 324/692 |
| 5,432,086 | 7/1995 | Franzl et al. ............................ 435/291 |

FOREIGN PATENT DOCUMENTS

| | | | |
|---|---|---|---|
| 2747033 | 4/1978 | Germany ............................. 435/287.1 |
| 2-057954 | 2/1990 | Japan ....................................... 435/39 |
| 92/16835 | 10/1992 | WIPO ................................. 435/287.1 |
| 93/19199 | 9/1993 | WIPO ..................................... 435/39 |

OTHER PUBLICATIONS

Richards, J.C.S., et al., Electronic measurement of bacterial growth, *J. Phys. E: Sci. Instrum.*, 1978, vol. II, pp. 560–568.

Kell, D.B., The principles and potential of elecrical admittance spectroscopy: an introduction, *Biosensors, Fundamentals and Applications*, Oxford University Press, 1987.

Silverman, M.P., et al., Automated electrical impedance technique for rapid enumeration of fecal coliforms in effluents from sewage treatment plants, *Appl. Env. Mic.*, Mar. 1979, pp. 521–526.

Henschke, P.A., Detection of wine–spoiling yeasts by electronic methods, *Journal of Applied Bacteriology*, 1988, 64, 123–133.

Hagan, D., Electrical measurement of bacterial growth, *Probiotech*, Feb. 1990, pp. IV–V.

Malthus—Technical Data, Malthus 2000 Incubator, Malthus Instruments Ltd., West Sussex, England. No Date Provided.

Macdonald, J.R., *Impedance Spectroscopy: Emphasizing solid materials and systems*, John Wiley & Sons, New York, 1987.

Fung, *Rapid methods for food microbiology*, pp. 16–21. No Date Provided.

*Primary Examiner*—William H. Beisner
*Attorney, Agent, or Firm*—Abelman, Frayne & Schwab

[57] ABSTRACT

A method for determining the number of microorganisms in a liquid sample, including the steps of dividing the liquid sample into a plurality of separate sub-samples, measuring the magnitude of at least one impedance component across each of the sub-samples and determining the number of the sub-samples for which the measured magnitude of the at least one impedance component indicates microorganism growth. The method preferably further includes the steps of applying A.C. voltage at a plurality of frequencies across at least a portion of the sample and measuring the at least one impedance component in response to at least some of the plurality of A.C. frequencies.

3 Claims, 8 Drawing Sheets

METHOD FOR ENUMERATING BACTERIAL POPULATIONS

FIELD OF THE INVENTION

The present invention relates to monitoring of microorganism populations in general and, more particularly, to testing liquid samples of mass produced food products, such as ultra high temperature (U.H.T) milk.

BACKGROUND OF THE INVENTION

Devices for determining the microorganism population in a sample, such as a U.H.T. milk sample, are known in the art. Using approximations of the rate of growth of known bacterial populations, past populations are extrapolated based on respective present populations. For example, impedance measurements of a sample are carried out during growth of bacteria in the sample. As the bacteria population in the sample grows and metabolizes, the ionic concentration of the sample changes and the electrical properties of the sample, particularly its impedance, changes. By measuring the changes in impedance at a constant temperature one can estimate the number of microorganisms.

However, in addition to inevitable error resulting from the above mentioned extrapolations, existing methods and devices for monitoring bacteria populations are generally extremely inaccurate and require a long incubation and monitoring period before conclusive results are reached. That is because significant changes in the electrical properties of the inoculated sample, which can not be attributed to non-bacterial activity in the sample, occur only at high microorganism concentrations. Since longer incubation periods are required in order to obtain high microorganism concentrations, extrapolations are made over longer time periods and, thus, the extrapolated results are considerably less accurate.

A common approach for determining the bacterial population of liquid samples, particularly U.H.T. milk samples, is based on impedance measurements across the sample. Since the impedance of a sample generally decreases as the bacterial population grows, impedance measurements across the sample provide a basis for estimating the bacterial population in the sample.

For impedance measurements in liquid samples, A.C voltage rather than D.C. voltage is generally provided to electrodes in the sample, since D.C. voltage tends to cause rapid, insulative, polarization at the interface between the liquid and the electrodes. When high frequency A.C. voltage, typically 1 KHz or more, is used, the effect of such polarization on the measured impedances is greatly reduced. Existing microorganism counting devices typically use 1 KHz or 10 KHz A.C. voltage.

Unfortunately, existing bacteria growth testers are inaccurate and require long incubation periods to provide reasonable results. This is due mainly to the fact that significant impedance changes, typically several percent, appear only after long incubation periods, when very high bacterial concentrations, typically over 1,000,000 bacteria per cubic centimeter, are reached. In addition to their low sensitivity to changes in small bacterial populations, existing testers are extremely sensitive to temperature changes in the sample which effect both the growth rate of the bacterial population and, more importantly, the magnitude of the measured impedances. Furthermore, since evaluation of past populations is generally based on measurement of the sample at the start of incubation as a reference and no reference is available at the time of testing, a high detection threshold is required even when the temperature is strictly stabilized.

A method of detecting bacteria in a wine sample by measuring the impedance of the sample is described in P. A. Henschke & D. Susan Thomas, "Detection of Wine-Spoiling Yeasts by Electronic Methods", Journal of Applied Bacteriology 1988, Volume 64, pp. 123–133. This article suggests the use of a chamber containing a sterilized medium as reference to the tested wine sample. Reference to the sterilized medium compensates for changes in the impedance of the wine sample due to physical and chemical factors not related to microbial growth. To distinguish between wine-spoiling yeasts and non-wine-spoiling yeasts, this, article explores the possibility of retarding the microbial growth in the non-wine-spoiling yeasts using ethanol.

There are various bacteria monitoring devices which are adapted for accommodating a plurality of liquid samples, wherein each sample is provided with a pair of electrodes for driving current therethrough. Such devices, typically referred to as multi-sensor impedance measuring devices, are useful for monitoring of a plurality of liquid samples, simultaneously. Examples of such multi-sample testers are described in U.S. Pat. Nos. 3,743,581, 3,890,201 and 4,072,578.

The devices of U.S. Pat. Nos. 3,743,581, 3,890,201 and 4,072,578 include a plurality of individual chambers for accommodating a respective plurality of separate inoculated samples. The device described in U.S. Pat. No. 4,072,578 also includes computerized means for controlling the bacterial growth analysis of the separate chambers.

A multi-chamber testing device based on the principles described above is commercially available from Malthus Instruments Ltd., England, under the trade name of Malthus 2000 Microbiology System. This device measures the conductance of up to 240 separate samples by providing 10 KHz A.C. voltage across electrodes associated with the samples. Microbial growth in each sample is detected by measuring changes in the conductance of a base which absorbs metabolic $CO_2$, using a computerized microbiological analyzer.

It should be appreciated, however, that the above mentioned deficiencies of existing single chamber devices, e.g. a low sensitivity which results in poor accuracy and which requires long testing periods, also apply to each chamber of existing multi-chamber devices. It should also be appreciated that none of the existing multi-chamber devices allow accurate detection of a small number of microorganisms in liquid samples.

It is appreciated that electrical property analysis techniques, particularly impedance spectroscopy, have improved considerably in the last decade. Thus, by constructing appropriate empirical models of the electrical behavior of a sample, i.e. constructing equivalent circuits of the sample, and by applying more automated and more accurate impedance measurement techniques, more conclusive evaluation of electrical-related properties of samples may now be possible. A general outline of the field of impedance spectroscopy can be found in J. Ross Macdonald, "Impedance Spectroscopy, Emphasizing solid materials and systems", New York, 1987. Bio-analytical applications of impedance spectroscopy can be found in Douglas B. Kell, "The Principles and Potential of Electrical Admittance Spectroscopy: an Introduction", from "Biosensors, Fundamental and Applications", edited by Anthony P. F. Turner et. al., Oxford University Press, 1987.

SUMMARY OF THE INVENTION

The present invention seeks to provide a significantly improved device for supervising the microorganism population in a sample using impedance analysis. First, the present device requires shorter monitoring and incubation periods than prior art devices. Second, the present device is capable of very accurately measuring extremely small microorganism populations, even one or two bacteria in a sample. Third, in a preferred embodiment of the invention, the device is particularly suitable for testing liquid samples of mass production processes, such as the production of ultra high temperature (UHT) milk.

According to one aspect of the present invention, a liquid sample to be tested is divided into a plurality, n, of sub-samples, contained in n, respective, separate cells. Each cell is associated with electrodes for applying an A.C. voltage of a preselected frequency across the sub-sample. When the microorganism population in the sample is small, typically when the number of microorganisms in the sample, M, is smaller than n, some of the sub-samples contain microorganisms and some sub-samples do not. The sub-samples containing microorganisms will be hereinafter referred to as inoculated samples. Statistically, when n is sufficiently larger than M, each inoculated sub-sample contains a single microorganism.

It has been found by the present inventor that using the above described sub-sample configuration, it is possible to detect the presences of a single microorganism in an inoculated sub-sample by sensing a change in the impedance of the sub-sample due to subsequent growth of the microorganism after incubation. Thus, according to this aspect of the invention it is possible to virtually count the number of organisms in the sample.

The sub-sample configuration also reduces the incubation periods which were previously required in order to obtain detectable populations. In a preferred embodiment of the invention, the sub-samples which do not contain any microorganisms, are used as reference sub-samples. The reference sub-samples, which are tested under the same environmental conditions, particularly the same temperature, as those of the inoculated sub-samples, provide an ideal reference to measurements performed on the inoculated sub-samples. Preferably, the impedance of each sub-sample is normalized based on its initial value to improve the accuracy of the reference. This increases the measurement accuracy considerably and, consequently, reduces the testing period required for obtaining significant results. Typically, a drop of approximately 0.1 percent or less in impedance, due to bacterial growth, will be sufficient for detection of the bacteria, in contrast to the several percent drop required by prior art devices.

According to another aspect of the present invention, particularly suitable for samples containing large bacterial populations, i.e. when M is considerably larger than n, the bacterial growth in some of the sub-samples is suppressed, for example by sterilization. The suppressed sub-samples are used as reference sub-samples for impedance analysis of the sub-samples which are not suppressed.

According to yet another aspect of the present invention, the electrodes associated with the n cells are configured and electrically connected such that only 2√n conductors and respective switches are required for separately addressing all the electrodes. This improvement of the present invention with respect to prior art multi-chamber devices, which typically required n+1 conductors and n switches, is particularly significant when the number of cells, n, is large.

In a preferred embodiment of this aspect of the invention, the sub-samples are matrix addressed via a plurality of conducting rows and a plurality of conducting columns, wherein each sub-sample is electrically associated with one row and one column. A three terminal or a five terminal impedance measurement circuit is preferably used for separately measuring the sub-sample impedances, whereby all the rows and columns not associated with a measured sub-sample are connected to a common potential, preferably a ground potential.

It should be appreciated that this aspect of the present invention, i.e. matrix addressing impedance measurement, is applicable to any situation in which a plurality of impedances are measured separately and, thus, suitable for applications other than microbial growth detection, According to yet another aspect of the present invention, the measured impedances are decomposed, by appropriate circuitry, into predefined real and/or imaginary, i.e. complex, components. The present inventor has found that some of these components are more sensitive than the total impedance of the sample to changes in the bacterial population in the sample. Preferably, according to this aspect of the present invention, the bacterial population in the sample is analyzed based on the more responsive component.

In accordance with one preferred embodiment of this aspect of the present invention, an embodiment which has been found suitable for UHT milk samples, the bacterial population analysis is based on measurement of the Warburg's impedance, an element of an equivalent circuit of UHT milk samples which is particularly sensitive to changes in the bacterial concentration of the milk.

BRIEF DESCRIPTION OF THE DRAWINGS

The present invention will be better understood from the following detailed description of preferred embodiments of the invention, taken in conjunction with the following drawings in which.

DETAILED DESCRIPTION OF A PREFERRED EMBODIMENT

Figure 1:
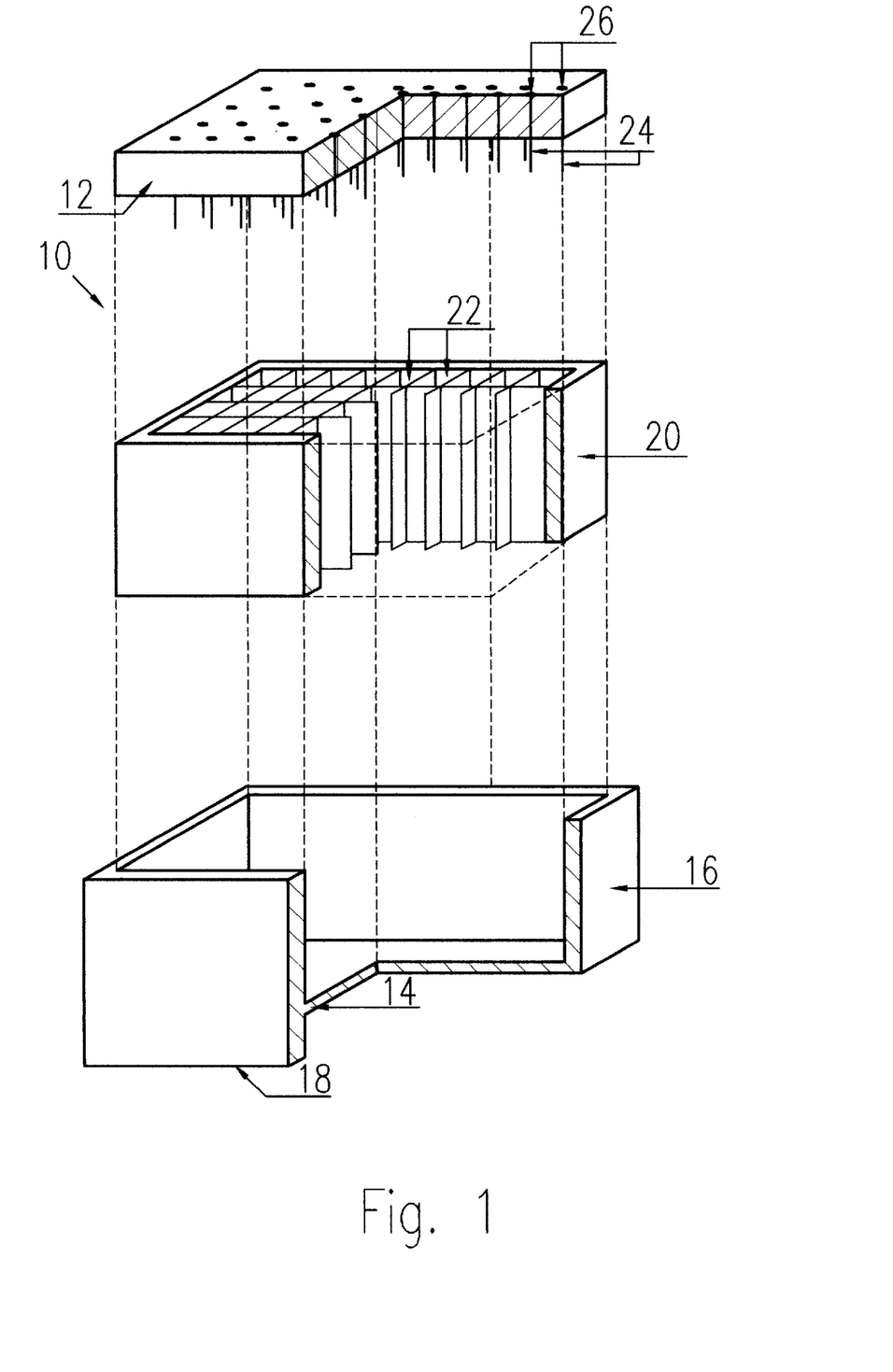
FIG. 1 is a schematic, partly cutaway, exploded, illustration of a multi-cell fixture for a bacteria population monitoring device, constructed in accordance with one preferred embodiment of the present invention.

Reference is now made to FIG. 1, which schematically illustrates a multi-cell fixture 10 for a bacteria population monitoring device, constructed and operative in accordance with one preferred embodiment of the present invention. Fixture 10 includes a liquid container 16, adapted for accommodating a liquid sample (not shown) such as ultra high temperature (UHT) milk, an individual cell-addressing top electrode arrangement 12 and a common cell-addressing bottom electrode 14. Bottom electrode 14, which preferably forms part of the bottom inside of container 16, may be electrically accessed through a single electric connection, for example through bottom terminal 18.

To enable division of the sample into sub-samples, as described below, fixture 10 further includes a multi-cell block 20 adapted for placement in container 16, between bottom electrode 14 and top electrode arrangement 12, and having a plurality of separate cells 22. To ensure separation between the different cells 22, a sealing member or arrangement (not shown) in the form of a grid, adapted for the cell division layout of block 20, is preferably provided at the interface between bottom electrode 14 and block 20. The volume of the liquid sample is preferably such that, when container 16 accommodates both the liquid sample and block 20, the level of liquid sample very nearly reaches the bottom surface of top electrode arrangement 12.

Block 20, particularly the walls separating cells 22, is preferably formed of an electrically non-conductive material such that the volumes of sample liquid in cells 22, hereinafter referred to as sub-samples, are maintained electrically isolated. As shown in FIG. 1, top electrode arrangement 12 includes a plurality of top electrodes 24 and respective electrical terminals 26, one electrode 24 and one terminal 26 for each cell 22. When top electrode arrangement 12 is placed on top of block 20, each top electrode 24 and its respective terminal 26 is associated with a respective cell 22 and the liquid sub-sample therein.

Figure 2:
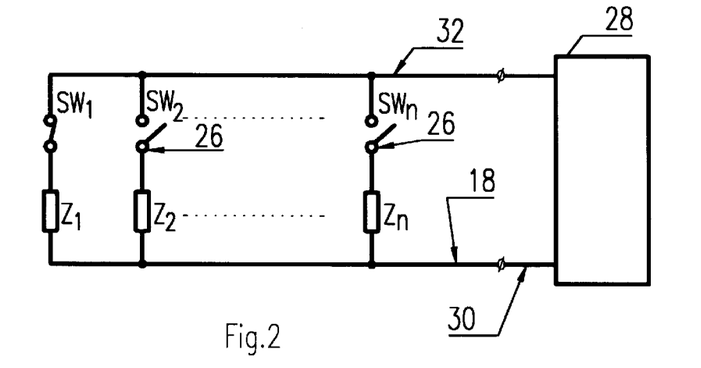
FIG. 2 is a schematic illustration of circuitry used in one, preferred, embodiment of the bacteria population monitoring device of FIG. 1.
Figure 3:
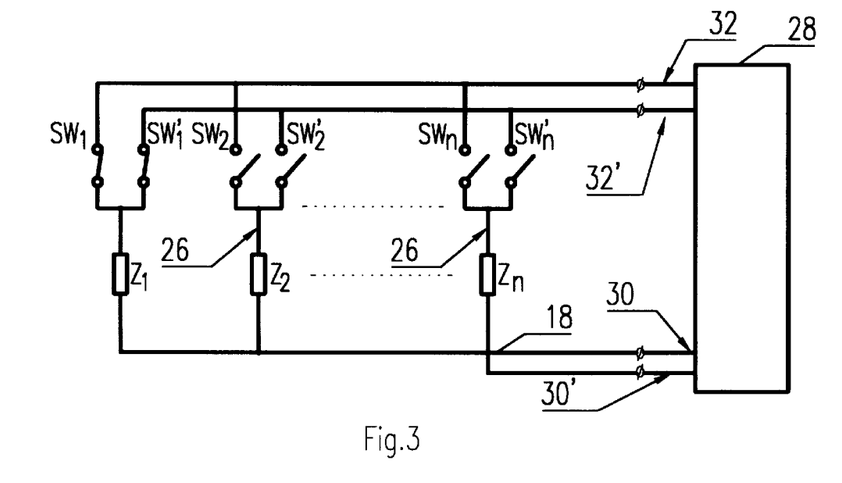
FIG. 3 is a schematic illustration of circuitry used in another, preferred, embodiment of the bacteria population monitoring device of FIG. 1.
Figure 4:
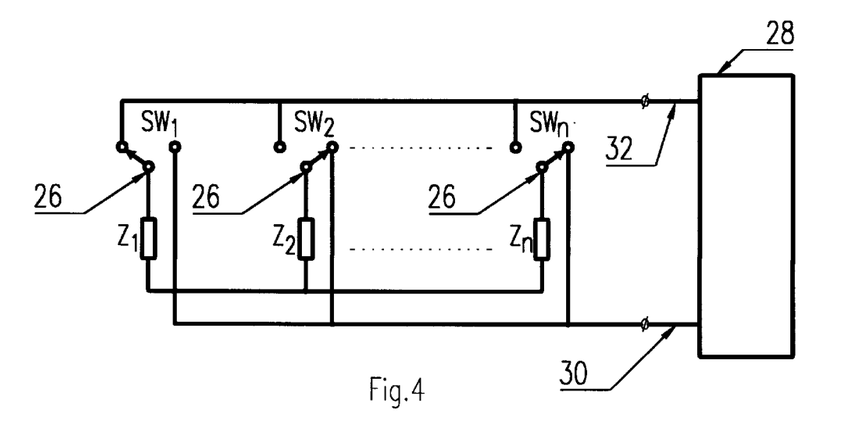
FIG. 4 is a schematic illustration of circuitry used in yet another, preferred, embodiment of the bacteria population monitoring device of FIG. 1.

Reference is now made also to FIGS. 2–4 which schematically illustrate three, alternative, electrical circuits for separately measuring the impedances of the sub-samples in cells 22. It should be appreciated that using fixture 10, as described above, the impedance of any one of the separate sub-samples can be measured by connecting only its terminals 26 to an impedance processor 28, as described below, which is also connected to terminal 18 of bottom electrode 14. The impedances of the separate sub-samples in cells 22 will be hereinafter denoted $Z_1, Z_2, \ldots, Z_n$, wherein n is the number of cells 22.

FIG. 2 shows one, alternative, circuit for separately measuring the impedances of the sub-samples in cells 22, i.e. impedances $Z_1, Z_2, \ldots, Z_n$. One terminal of impedance processor 28 is connected through a first conductor 30 to bottom electrode 14, which is associated as described above with the sub-samples in all of cells 22.

A second conductor 32 connects another terminal of impedance processor 28 to connections 26 of all of top electrodes 24, through respective switches $SW_1, SW_2, \ldots, SW_n$, thereby forming n parallel, separately addressed, measurement branches having the impedances $Z_1, Z_2, \ldots, Z_n$, respectively. Switches $SW_1, SW_2, \ldots, SW_n$, which may be contact or non-contact switches, are preferably activated in accordance with a preselected activation sequence by appropriate control circuitry in impedance processor 28, so as to periodically measure the impedances.

FIG. 3 shows an alternative circuit for separately measuring the impedances of the sub-samples in cells 22, in which a four terminal connection scheme is employed. A four terminal connection is preferred, since impedances $Z_1, Z_2, \ldots, Z_n$ must be measured very accurately. In this circuit, two additional terminals of impedance processor 28 are connected to bottom electrode 14 and top electrodes 24 via a third conductor 30' and a second conductor 32', respectively. According to this scheme, impedance processor 28 provides a preselected top potential $V_t$ via conductor 32' and a preselected bottom potential $V_b$ via conductor 30. As known in the art, potentials $V_t$ and $V_b$ compensate for the undue influence of the impedances of the different conductors, switches and electrodes included in the system.

Impedances $Z_1, Z_2, \ldots, Z_n$ are separately connected between potentials $V_t$ and $V_b$ via respective switches $SW'_1, \ldots, SW'_n$. Switches $SW'_1, \ldots, SW'_n$ are preferably activated in accordance with a preselected activation sequence by the control circuitry in impedance processor 28.

FIG. 4 shows yet another alternative circuit for separately measuring the impedances of the sub-samples in cells 22, while avoiding direct connection between bottom electrode 14 and impedance processor 28. According to this scheme, the sample in container 16 acts as a common bottom electrode, in place of bottom electrode 14. This may be achieved, for example, by leaving a gap between the bottom of container 16, i.e. electrode 14, and multi-cell block 20. It will be appreciated by persons skilled in the art that a four terminal connection variant (not shown) based on the circuit of FIG. 4, analog to the four terminal connection of FIG. 3, may be readily constructed.

FIG. 4 depicts, as an example, a situation in which only impedance $Z_1$ is measured by impedance processor 28. Switch $SW_1$ connects impedance $Z_1$ to conductor 32, while the impedances of the remaining parallel branches, $Z_2, Z_3, \ldots, Z_n$, are connected via switches $SW_2, SW_3, \ldots, SW_n$ to conductor 30. Thus, in the example of FIG. 4, impedance processor 28 measures impedance $Z_1$ in series with the parallel equivalent of impedances $Z_2, Z_3, \ldots, Z_n$. The total impedance measured by impedance processor 28 is therefore:

$$Z = Z_1 + (Z_2 + Z_3 + \ldots + Z_n)/(n-1).$$

If n is sufficiently large, as is preferably the case, the contribution of second component, i.e. the parallel equivalent of the remaining impedances, is negligible and, thus, hardly affects the measurement of impedance $Z_1$. This is because the absolute value of the second impedance component is n−1 times smaller than $Z_1$. Therefore, in the example of FIG. 4, $Z \approx Z_1$.

It should be appreciated that the remaining impedances can be measured in a similar manner. For example:

$$Z_2 \approx Z_2 + (Z_1 + Z_3 + \ldots + Z_n)/(n-1),$$

and so on.

The accuracy of the impedance measurements described above will generally be affected by factors, such as the resistance of the electrodes, the environmental temperature and the volume of the sub-samples in cells 22. These systematic factors have been known to have a considerable effect on impedance measurement accuracy in all traditional methods and devices for monitoring microorganism populations by measuring impedance changes during microorganism growth. In accordance with a preferred embodiment of the present invention, multi-cell fixture 10 (FIG. 1) is kept in a temperature controlled environment suitable for microorganisms's growth. Due to the identical incubation conditions for all of the cells, when a given group of sub-samples all have the same number of microorganisms, for example one microorganism per sub-sample, the impedances across each sub-sample in the group is substantially the same. Similarly, when there are no microorganisms whatsoever in any sub-sample of a group of sub-samples, the impedance of each sub-sample in the group is substantially the same. This provides a reliable basis for using the impedances measured across some of the sub-samples, e.g. samples which are not: inoculated, as references for the impedances measured across other sub-samples, e.g. inoculated samples, as described in detail below.

In the present invention, the influence of the above mentioned factors is substantially reduced, partly since the influence of these factors on all the sub-samples is approximately the same. However, since there are other, non-systematic, factors which effect the impedance measurements, for example slight differences between the conductivity at the electrode interfaces of different cells 22, normalization of the measured impedances may be required. One example of such normalization is based on determining the relative change, $\delta Z_{it}$, in each sub-sample impedance $Z_i$, at a time, t, relative to the impedance of the same sub-sample, i, at an initial reference time, 0:

$$\delta Z_{it} = (Z_{i0} - Z_{it})/Z_{i0},$$

wherein:
$Z_{it}$–impedance of sub-sample i at time t.
$Z_{i0}$–impedance of sub-sample i at time 0, a reference point in time.

Since all sub-samples have substantially the same temperature, impedance measurements will not be affected by small, systematic, changes in temperature. Furthermore, since normalized impedances are preferably used, for example the $\delta Z_{it}$'s described above, the effect on measurement accuracy of physical differences between the elements associated with the different sub-samples is negligible. If, initially, the temperature in cells 22 is homogeneous and steady, differences in measurement conditions between different cells 22, e.g. electrode resistance and sub-sample volume, will not reduce the measurement accuracy as long as normalized impedances, such as the $\delta Z_{it}$s, are used. In a preferred embodiment of the present invention, appropriate circuitry in impedance processor 28, for example a subtracter, is used for calculating the $\delta Z_{it}$ values.

The remaining factors which may affect the measured impedances include growth of the microorganism population, changes in the structure of the sample with time and random errors in the impedance measurement. Since time changes in sample structure are substantially the same for all cells and since random errors in the impedance measurement are generally negligible compared to sample-related errors, the $\delta Z_{it}$ values are expected to be reliable indicators of the rate of microorganism growth.

In the existing methods and devices, the environmental temperature must be sustained at given values with great indicated accuracy, typically ±0.7° C. or more, and even greater short-term stability, typically ±0.06° C. or more, in order to obtain reasonable measurement accuracy. The present invention overcomes these strict requirements, by utilizing the impedances measured across some sub-samples as references for impedances measured across other sub-samples.

In accordance with the present invention, appropriate circuitry in impedance processor 28, for example a comparator, is used for comparing between the different $\delta Z_{it}$ values. Significant differences, i.e. differences beyond a preselected threshold, between the compared $\delta Z_{it}$ values of different sub-samples indicate a difference in microorganism growth between the sub-samples. Due to the extremely high accuracy obtained by the methods and devices of the present invention, a threshold difference of less than 0.1 percent between the impedances of two given sub-samples will be generally sufficient for significantly distinguishing between the two samples, in contrast to prior art devices which generally require a threshold of several percent. Since such differences can be detected at relatively low bacterial concentrations, a shorter pre-testing period is required.

It has been found by the present inventor that sub-samples containing bacteria can be significantly distinguished from sub-samples which do not contain bacteria by comparing their $\delta Z_{it}$ impedance values. When there are substantially less than n microorganisms in the entire sample, i.e. there are more cells 22 than microorganisms, the probability of more than one microorganism being in one cell 22 is very low. Thus, for small microorganism populations, the number of sub-samples containing microorganisms is practically equal to the number of microorganisms in the entire sample. Therefore, the present bacteria population monitoring device can practically count the number of microorganisms in the sample, when the microorganism population is sufficiently small. This counting function is preferably achieved by appropriate circuitry in impedance processor 28.

When the sample contains a large bacteria population, i.e. considerably larger than n, the number of bacteria in the sample can not be counted. However, by suppressing the bacterial growth in some of the sub-samples, for example by sterilization, the suppressed sub-samples can be used as reference sub-samples for impedance measurements of the remaining sub-samples which were not suppressed. It should be appreciated that such use of reference samples can also be applied to conventional impedance analysis devices, thereby to improve the accuracy of such devices. As described above, the measurement accuracy achieved by using such a reference scheme may improve the significant detection threshold of conventional devices from the traditional several percent to 0.1 percent or better, thereby shortening the testing periods required by such conventional devices.

Figure 5:
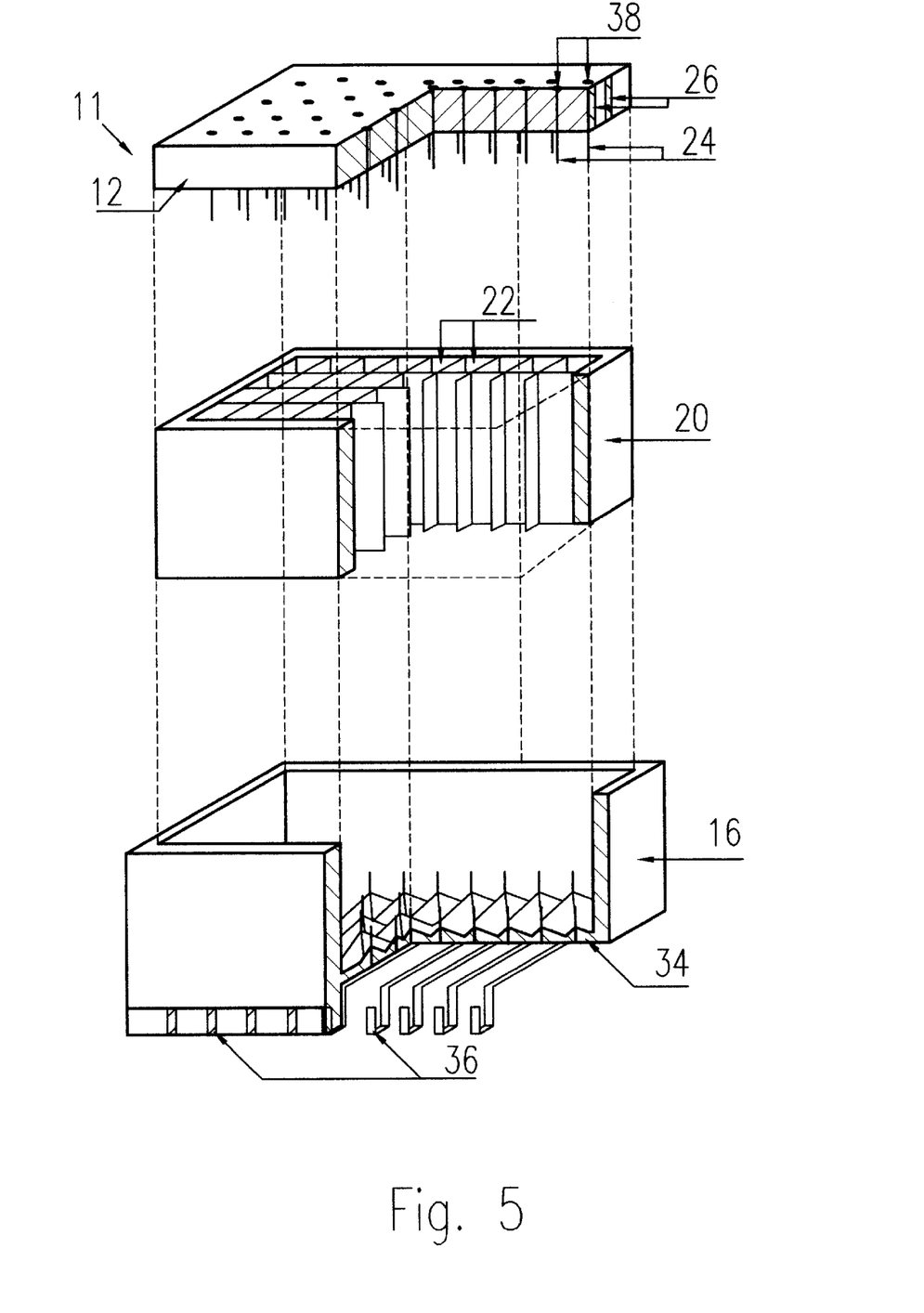
FIG. 5 is a schematic, partly cutaway, exploded illustration of a multi-cell fixture for a bacteria population monitoring device, constructed in accordance with another preferred embodiment of the present invention in which matrix addressing impedance measurement is employed.

Reference is now made to FIG. 5 which schematically illustrates an alternative multi-cell fixture 11, constructed and operative in accordance with a further preferred embodiment of the present invention. The fixture of FIG. 5 economizes on the number of conductors and switches required for separately connecting the sub-sample impedances $Z_1$, $Z_2$, ..., $Z_n$ to impedance processor 28. It is appreciated that in the embodiment of FIGS. 1–4, at least n+1 conductors and n switches are necessary for separately addressing all of top electrodes 24 (FIG. 1).

Multi-cell fixture 11 includes a plurality of parallel bottom terminal lines 36 and a plurality of parallel top terminal lines 38, which are preferably substantially perpendicular to bottom terminal lines 36. Lines 36 and 38 will be hereinafter referred to as rows 36 and columns 38, respectively. A plurality, n, of individual bottom electrodes 34, which are connected in series along rows 36, are mounted on the bottom surface of container 16 so as to be associated with respective cells 22. If the n lower electrodes 34 are arranged in a square array, as is preferably the case, the number of terminal connections needed for addressing all of rows 36 is $\sqrt{n}$.

Similarly, the n top electrodes 24 are connected in series along columns 38 via top connections 26. If the n top electrodes 24 are arranged in a square array, as is preferably the case, the number of terminal connections needed for addressing all of columns 38 is $\sqrt{n}$. It should be appreciated that according to this embodiment, in which bottom electrodes 34 are addressed through rows 36 and top electrodes 24 are addressed through columns 38, the total number of connections and switches required for addressing all of cells 22 is only $2\sqrt{n}$. This method of addressing the sub-samples will be hereinafter referred to as matrix addressing, since it is similar to matrix addressing as used in other fields. The impedance of a sub-sample connected between top column i and bottom row j will be hereinafter denoted $Z_{i-j}$.

Figure 6A:
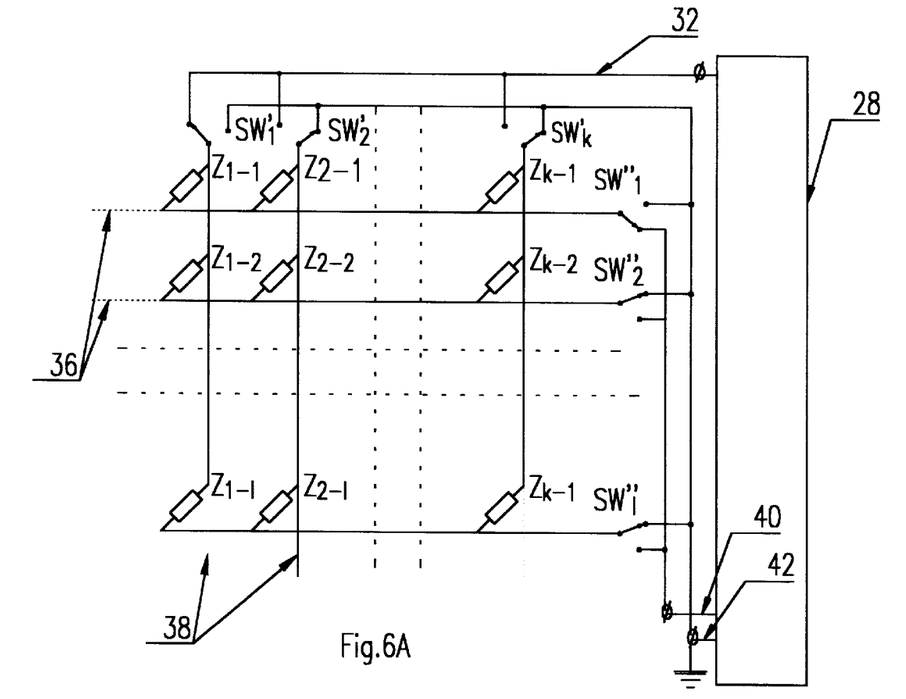
FIGS. 6A and 6B are schematic illustrations of addressing circuitry used in a preferred embodiment of the bacteria monitoring device of FIG. 5.

FIG. 6A shows a preferred circuit for matrix addressing of impedances $Z_{1-1}, Z_{2-1}, \ldots, Z_{k-l}$ by impedance processor 28, via l bottom rows and k top columns. Switches $SW'_1$, $SW'_2, \ldots, SW'_k$ are operative for connecting each of top columns 38 either to top conductor 32 or to a common conductor 42 which is connected to a ground terminal of impedance processor 28. Switches $SW''_1, ''_2, \ldots, SW''_l$ are operative for connecting each of bottom rows 36 to either a bottom conductor 40 of impedance processor 28 or with common conductor 42. Impedance $Z_{i-j}$, for example, is measured when switches $SW'_i$ and $SW''_j$ are switched to top conductor 32 and bottom conductor 40, respectively, while the remaining SW' and SW'' switches are switched to common conductor 42, which is grounded as described above.

Conductors 32, 40 and 42 are preferably connected to a three terminal impedance measurement circuit, in impedance processor 28, which enables the matrix addressing impedance measurement as described in detail below. It will be appreciated by persons skilled in the art that a five terminal circuit (not shown) may be readily constructed based on the three terminal circuit shown in FIG. 6A.

Figure 6B:
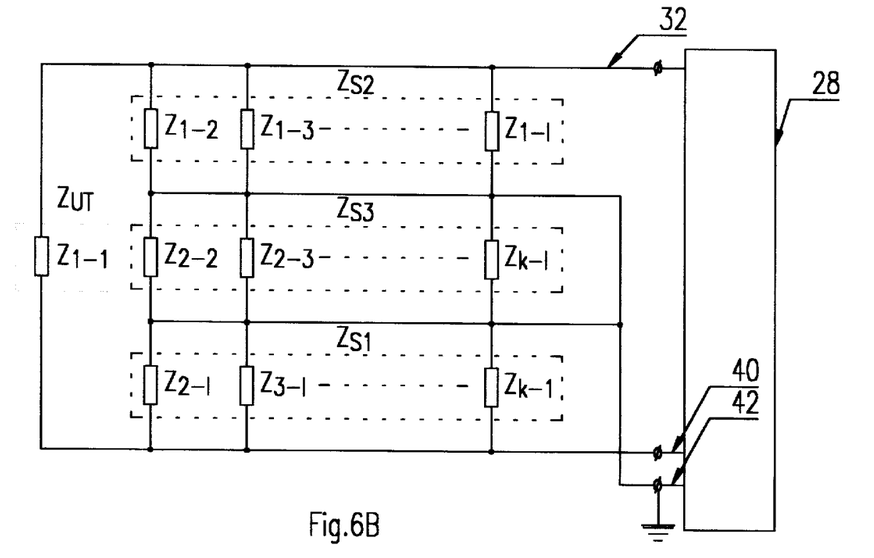

The circuit of FIG. 6B is equivalent to the circuit of FIG. 6A with switches SW' and SW'' switched for measuring impedance $Z_{1-1}$. The remaining impedances $Z_{2-1}, \ldots, Z_{k-l}$, which are all connected to common conductor 42, have substantially no effect on the measurement of $Z_{1-1}$, due to the three-terminal impedance measurement circuitry used by impedance processor 28, as described below with reference to FIGS. 7A and 7B.

Figure 7A:
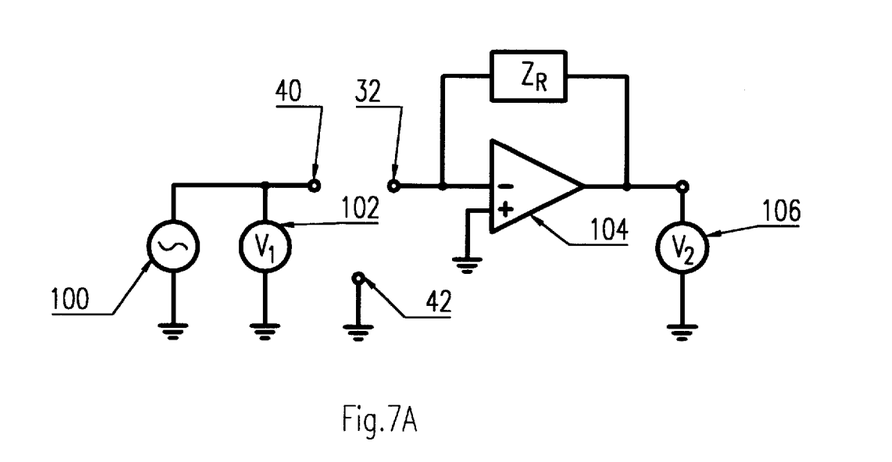
FIG. 7A is a schematic illustration of impedance measurement circuitry used in a preferred embodiment of the bacteria monitoring device of FIG. 5.

FIG. 7A schematically illustrates the three terminal impedance measurement circuitry, which is particularly suitable for the matrix addressing embodiment of FIGS. 5, 6A and 6B. The three-terminal impedance measurement circuitry preferably includes an A.C. power source 100, a first voltmeter 102, an operational amplifier 104 and a second voltmeter 106. A.C. power source 100 generates an input voltage, $V_1$, at preselected A.C. frequencies between top conductor 40 and the ground. Input voltage $V_1$ is measured by first voltmeter 102. One of the input terminals of amplifier 104, preferably its negative terminal is connected to top conductor 32 and the output terminal of amplifier 104 is grounded through second voltmeter 106 which, therefore, measures an output voltage, $V_2$. The other input terminal of amplifier 104, preferably its positive terminal, is grounded. A reference impedance $Z_r$, preferably a resistor, is connected in parallel with operational amplifier 104.

Figure 7B:
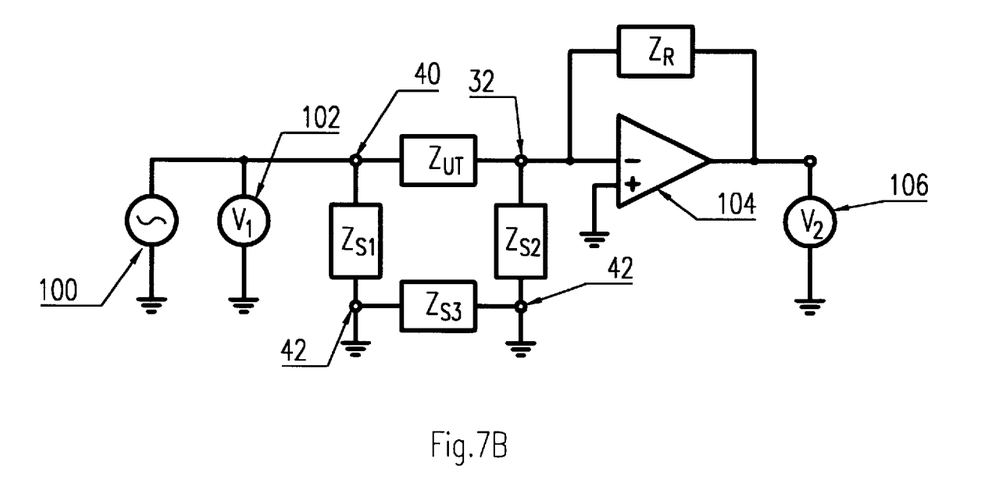
FIG. 7B is a schematic illustration of an equivalent circuit corresponding to the circuitry of FIGS. 6B and 7A.

Reference is now also made to FIG. 7B which schematically illustrates an equivalent circuit of the three terminal impedance measurement circuitry of FIG. 7A when connected to the addressing circuitry of FIG. 6B. The equivalent circuit of FIG. 7B includes an impedance under test, $Z_{ut}$, which is equal to $Z_{1-1}$ in the example of FIG. 6B, and shunt impedances $Z_{s1}$, $Z_{s2}$ and $Z_{s3}$ which represent three, respective, branches of parallel sub-sample impedances, as seen in FIG. 6B. Impedance $Z_{ut}$ is connected between bottom conductor 40 and top conductor 32, shunt impedance $Z_{s1}$ is connected between bottom conductor 40 and common conductor 42, shunt impedance $Z_{s2}$ is connected between top conductor 32 and common conductor 42 and both terminals of shunt impedance $Z_{s3}$ are connected to common conductor 42. As mentioned above, common conductor 42 is preferably grounded.

It will be appreciated that the voltage across $Z_{s2}$ is substantially zero, since it is connected between the grounded common conductor 42 and a substantially zero potential, i.e. a virtual ground, at the negative input of amplifier 104 and, therefore, impedance $Z_{s2}$ draws substantially zero current. Thus, the current flowing through impedance $Z_{ut}$ is substantially equal to the current flowing through reference impedance $Z_r$. Thus, the following equation holds:

$$V_1/Z_{ut} \approx -V_2/Z_r \qquad (1)$$

It should be appreciated that the current drawn by impedance $Z_{s1}$ does not affect equation (1), since the voltage drop between power source 100 and bottom conductor 40 is substantially zero. Since impedance $Z_r$ is known and voltages $V_1$ and $V_2$ are measured by voltmeters 102 and 106, impedance $Z_{ut}$ is readily determined. This provides an accurate measurement of the impedance across each sub-sample using the above mentioned matrix addressing.

Figure 8:
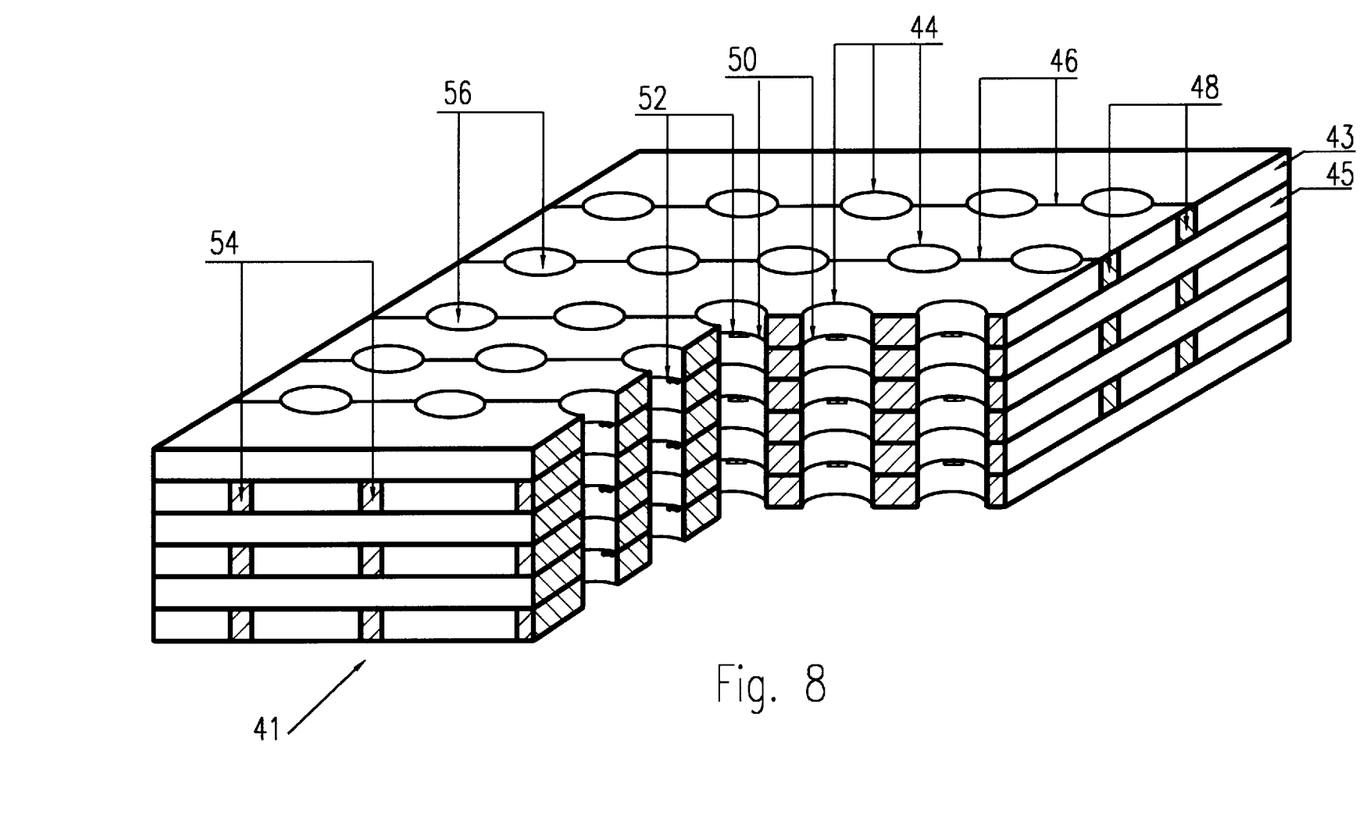
FIG. 8 is a schematic, partly cutaway, illustration of a multi-layer, multi-cell, fixture for a bacteria population monitoring device, constructed in accordance with yet another, preferred, embodiment of the present invention.

FIG. 8 schematically illustrates a multi-layer, multi-cell, fixture 41, used in a further preferred embodiment of the present invention. Fixture 41 is adapted to increase the number of sample regions measured by impedance processor 28. In this preferred embodiment of the invention, each sub-sample is associated with a plurality of pairs of electrodes, thereby enabling measurement of impedances of different levels within a plurality of cells 56. The number of electrodes associated with each cell 56 is determined by the number of layers in fixture 41.

A top layer 43 of fixture 41 includes top electrode connections 44 connected along parallel conducting columns 46, similar to columns 38 of FIG. 5. Columns 46 are addressed through terminals 48. Top layer 43 also includes bottom electrode connections 50 connected along parallel conducting rows 52. Rows 52 are addressed through terminals 54.

According to this embodiment of the present invention, bottom electrode connections 50 serve also as top electrode connections for the next layer 45 underneath top layer 43. Thus, the top electrode connections of layer 45 are connected by conducting rows, while the bottom electrode connections of layer 45 are connected by conducting columns. The relationship between any other adjacent layers is the same as the relationship described above between layer 43 and layer 45.

The electrodes of each layer of fixture 41 can be addresses by a circuit similar to that of FIGS. 6 and 7. Thus, by constructing a circuit which is equivalent to a plurality of circuits as in FIGS. 6 and 7, connected in parallel, it is possible to address the different levels in cells 56 by using matrix addressing as described above in each level.

Figure 9:
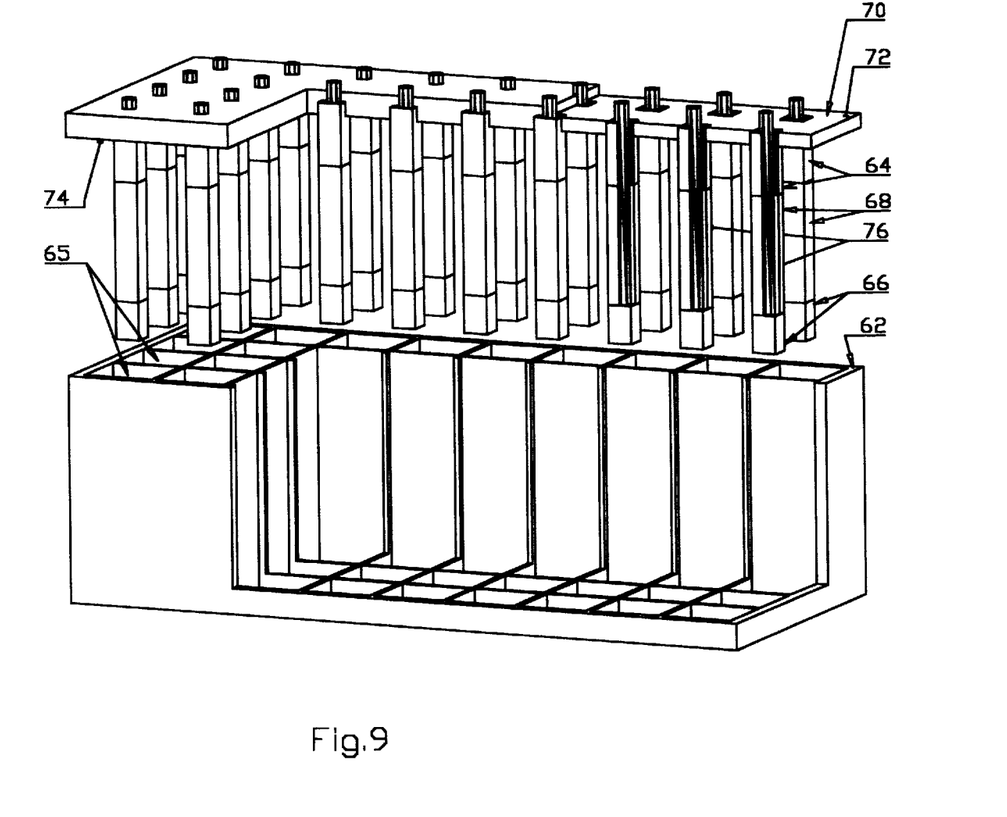
FIG. 9 is a schematic, partly cutaway, exploded. illustration of an electrode connection scheme for a multi-cell bacteria monitoring device, according to a preferred embodiment of the present invention.
Figure 10A:
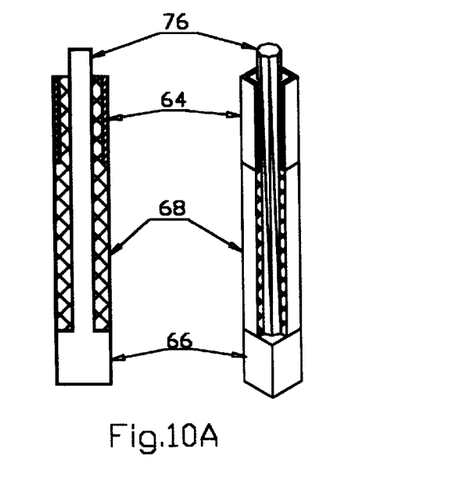
FIG. 10A is a schematic illustration of the electrode connections of one cell in the scheme of FIG. 9.

Reference is now made to FIG. 9 which schematically illustrates yet another, preferred, multi-cell fixture 60. Fixture 60 preferably includes a multi-cell block 62, similar to block 20 of FIGS. 1 and 5, which comprises a plurality of cells 65 similar to cells 22 of FIGS. 1 and 5. FIG. 10A illustrates in more detail the electrode arrangement in each of cells 65.

In contrast to the fixtures of FIGS. 1 and 5, fixture 60 has no electrical connections underneath block 62. Rather, bottom electrodes 66 are physically connected to respective top electrodes 64 by means of non-conductive rods 68. Electric connection between bottom electrodes 66 and conducting rows 74, which are located in a top electrode arrangement 70, is provided by respective extension wires 76. Top electrodes 64 are connected to conducting columns 72 in top electrode arrangement 70. Rows 74 and columns 72 connected to impedance processor 28 via conductors (not shown) similar to conductors 32 and 40, which connect rows 36 and columns 38 to impedance processor 28 in the embodiment of FIGS. 5–7.

In a variation of this embodiment of the invention, not shown in the drawings, a plurality of electrodes are mounted at different levels along each of rods 68, thereby to increase the number of separate impedance measurements. Electrical connections to such an arrangement may be provided as described above with reference to the multi-layer fixture of FIG. 8.

Figure 10B:
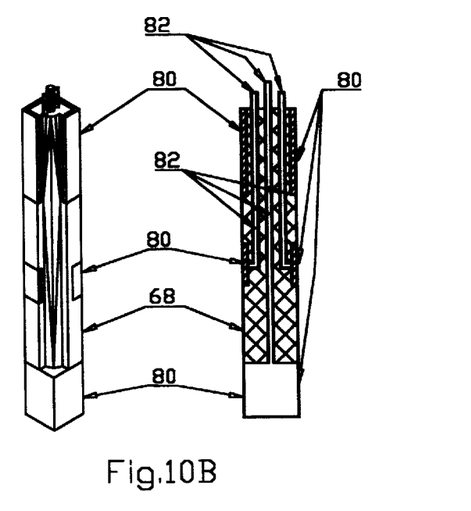
FIG. 10B is a schematic illustration of alternative, multi-level, electrode connections of the cells in the scheme of FIG. 9.

FIG. 10B schematically illustrates a preferred multi-layer electrode arrangement for each of cells 65. As shown in FIG. 10B, a plurality of electrodes 80 are positioned at preselected levels along each of rods 68. Electrodes 80 are preferably connected, preferably via respective extension wires 82, to an addressing network including interlaced conducting rows and columns (not shown), similar to that of FIG. 8, which may be connected to impedance processor 28 as described above with reference to FIG. 8.

Since evaporation of the liquid sample may have some effect on measurement accuracy, all the above described multi-cell fixtures are preferably provided with sealing members for substantially sealing the sample from the external environment, during operation. In particular, a sealing member (not shown) is preferably provided between the top of container 16 and top electrode arrangement 12 (FIGS. 1 and 5). Additionally, portions of top electrode arrangement 12, or 70 in the embodiment of FIG. 9, which are not immersed in the liquid sample during normal operation of the present device, are preferably electrically insulated from the external environment.

It has been found by the present inventor that more sensitive measurements can be obtained by the device of the present invention if only a particular component of the sub-sample impedances is measured by impedance processor 28, rather than the total impedance of the sub-samples. To synthesize a desired impedance component, it is necessary to construct an equivalent electrical circuit of the sample being tested, in which the desired impedance is included as a distinct circuit element.

Since the impedance of the equivalent circuit, by definition, is equivalent to the impedance of the sample being tested, one can construct a set of linear or non-linear equations, depending on the sample material, by measuring the sample impedance at a plurality of A.C. frequencies. The number of impedance measurements needed corresponds to the number of unknowns in the equivalent circuit. In a preferred embodiment of the present invention, a plurality of A.C. frequencies in the range of approximately 10 Hz to approximately 10 MHz are used, in contrast to prior art devices which use a constant frequency, typically 1 KHz or 10 KHz.

For an outline on equivalent circuits in impedance spectroscopy see J. Ross Macdonald, "Impedance Spectroscopy, Emphasizing solid materials and systems", N.Y., 1987. On equivalent circuits of microorganism growth see J. C. S. Richard, A. C. Jason, G. Hobbs, D. M. Gibson and R. H. Christie, "Electronic Measurement of Bacterial Growth", Journal of Physics and Electronics: Scientific Instruments, Volume II, 1978.

Figure 11:
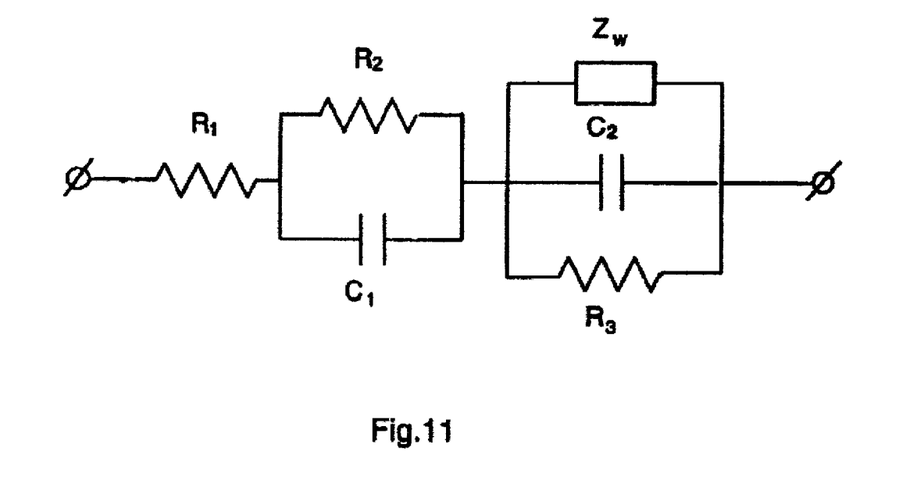
FIG. 11 is a schematic illustration of a preferred equivalent electric circuit of ultra high temperature (UHT) milk.

FIG. 11 illustrates a preferred equivalent circuit for UHT milk samples. As can be seen in FIG. 11, the preferred equivalent circuit includes three resistors, $R_1$, $R_2$ and $R_3$, two capacitors, $C_1$ and $C_2$ and one component, denoted $Z_W$, known as Warburg's Impedance. Warburg's impedance, as known in the art, is given by the following equation:

$$Z_W = W(1-j)/(2\pi f)^{1/2},$$

wherein:
$Z_W$ is Warburg's impedance;
W is Warburg's variable;
j is the imaginary impedance notation; and
f is the A.C. frequency which is used.

It has been found by the present inventor that Warburg's Impedance is at least ten times more sensitive to changes in the number of bacteria in UHT milk than the total impedance of the circuit. Therefore, in a preferred embodiment of the invention, appropriate circuitry in impedance processor 28 synthesizes Warburg's Impedance, by measuring the impedance of a UHT milk sample in response to several A.C. frequencies, as described above, and by subsequently solving a set of non-linear equations.

It should be appreciated that other impedance components may be found to be equally significant or even more significant than Warburg's Impedance in detecting bacterial growth in other materials. Thus, the present invention is not limited to measurement of the specific impedance components described above for the purposes described above but, rather, to measurement of any component which may be found suitable for detecting and/or evaluating given bacteria related phenomena.

It will be appreciated by persons skilled in the art that the present invention is not limited to what has been thus far described. Rather, the scope of the present invention is limited only by the following claims:

I claim:

1. A method for determining the number of microorganisms in a liquid sample comprising:

dividing a known volume of a liquid sample into a plurality of separate sub-samples, wherein it is known that the liquid sample contains a number of microorganisms which is substantially less than the number of sub-samples;

measuring the magnitude of at least one impedance component across each of the sub-samples; and determining the number of the sub-samples for which the measured magnitude of the at least one impedance component is lower, by a preselected difference, from the at least one impedance component measured across others of the sub-samples, the number of sub-samples for which the measured magnitude of the at least one impedance component is lower, by a preselected difference, from the at least one impedance component measured across others of the sub-samples being an indication of the number of microorganisms in the liquid sample.

2. A method for evaluating the microorganism population in a plurality of separate liquid samples comprising:

connecting the plurality of samples to a plurality of conducting rows and a plurality of conducting columns such that each sample is row wise connected to a given row and column wise connected to a given column;

measuring the magnitude of at least one impedance component across a plurality of the samples; and evaluating the microorganism population in the samples based on the magnitude of the at least one impedance component measured across each sample, wherein, for each measured sample, measuring the magnitude of the at least one impedance component comprises:

grounding all rows and all columns other than the given row and the given column which are connected to the measured sample; and measuring the at least one impedance component between the given row and the given column which are connected to the measured sample.

3. A method for determining the number of microorganisms in a liquid sample comprising:

dividing a known volume of a liquid sample into a plurality of separate sub-samples, wherein it is known that the liquid sample contains a number of microorganisms which is substantially less than the number of sub-samples;

connecting the plurality of sub-samples to a plurality of conducting rows and a plurality of conducting columns such that each sub-sample is row wise connected to a given row and column wise connected to a given column;

measuring the magnitude of at least one impedance component across each of the sub-samples; and determining the number of the sub-samples for which the measured magnitude of the at least one impedance component indicates microorganism growth, the number of sub-samples for which microorganism growth is indicated being an indication of the number of microorganisms in the liquid sample, wherein, for each measured sub-sample, measuring the magnitude of at least one impedance component comprises:

grounding all rows and all columns other than the given row and the given column which are connected to the measured sub-sample; and measuring the at least one impedance component between the given row and the given column which are connected to the measured sub-sample.

\* \* \* \* \*